(12) United States Patent
Finocchiaro et al.

(10) Patent No.: US 8,574,291 B2
(45) Date of Patent: Nov. 5, 2013

(54) LINEAR DRIVE AND PUMP SYSTEM, IN PARTICULAR AN ARTIFICIAL HEART

(75) Inventors: Thomas Finocchiaro, Aachen (DE); Thomas Butschen, Viersen (DE); Marc Lessmann, Arnsberg (DE); Kay Hameyer, Heverlee (BE); Thomas Schmitz-Rode, Aachen (DE); Ulrich Steinseifer, Hauset (BE); Paul Barteld Kwant, AG Vijlen (NL)

(73) Assignees: Rheinisch-Westfaelische Technische Hochschule Aachen, Aachen (DE); Herz-und Diabeteszentrum NRW, Bad Oeynhausen (DE)

( * ) Notice: Subject to any disclaimer, the term of this patent is extended or adjusted under 35 U.S.C. 154(b) by 543 days.

(21) Appl. No.: 12/670,708

(22) PCT Filed: Aug. 18, 2008

(86) PCT No.: PCT/EP2008/006762
§ 371 (c)(1),
(2), (4) Date: Jun. 1, 2010

(87) PCT Pub. No.: WO2009/024308
PCT Pub. Date: Feb. 26, 2009

(65) Prior Publication Data
US 2010/0234941 A1 Sep. 16, 2010

(30) Foreign Application Priority Data
Aug. 17, 2007 (DE) .......................... 10 2007 039 014

(51) Int. Cl.
*A61M 1/10* (2006.01)
(52) U.S. Cl.
USPC ........................................ 623/3.11; 623/3.17

(58) Field of Classification Search
USPC ............................... 623/3.11, 3.17, 3.22, 3.27
See application file for complete search history.

(56) References Cited

U.S. PATENT DOCUMENTS

| | | | | |
|---|---|---|---|---|
| 5,300,111 | A * | 4/1994 | Panton et al. | 623/3.19 |
| 5,360,445 | A | 11/1994 | Goldowski | 623/3 |
| 5,924,975 | A | 7/1999 | Goldowski | 600/16 |
| 6,190,409 | B1 | 2/2001 | Vitale | 623/3.18 |
| 6,194,796 | B1 | 2/2001 | Yeakley | 310/14 |
| 6,600,399 | B1 | 7/2003 | Trandafir | 335/222 |
| 2002/0165425 | A1 * | 11/2002 | Yoon et al. | 600/16 |

FOREIGN PATENT DOCUMENTS

DE 10360713 7/2005

OTHER PUBLICATIONS

Machine translation of DE10360713. Date accessed Aug. 9, 2012.*

* cited by examiner

*Primary Examiner* — Thomas J Sweet
*Assistant Examiner* — Rebecca Preston
(74) *Attorney, Agent, or Firm* — Andrew Wilford

(57) ABSTRACT

The invention relates to an electrical linear drive, in particular for a pump system of an artificial heart, with a movable part and a stationary part, wherein the stationary part is formed by a permanent magnet arrangement and the movable part is formed by a coil arrangement, or vice versa, and wherein the coil arrangement and the permanent magnet arrangement can be moved to and fro relative to each other in an axial direction by means of current passed through the coil arrangement. The invention further relates to an electrical linear drive of this kind in which the permanent magnet arrangement is designed as a stack of frame-shaped, in particular ring-shaped magnets, which are magnetized alternately radially and axially in the axial direction, such that the magnetic field is strengthened on one side of the frame.

20 Claims, 5 Drawing Sheets

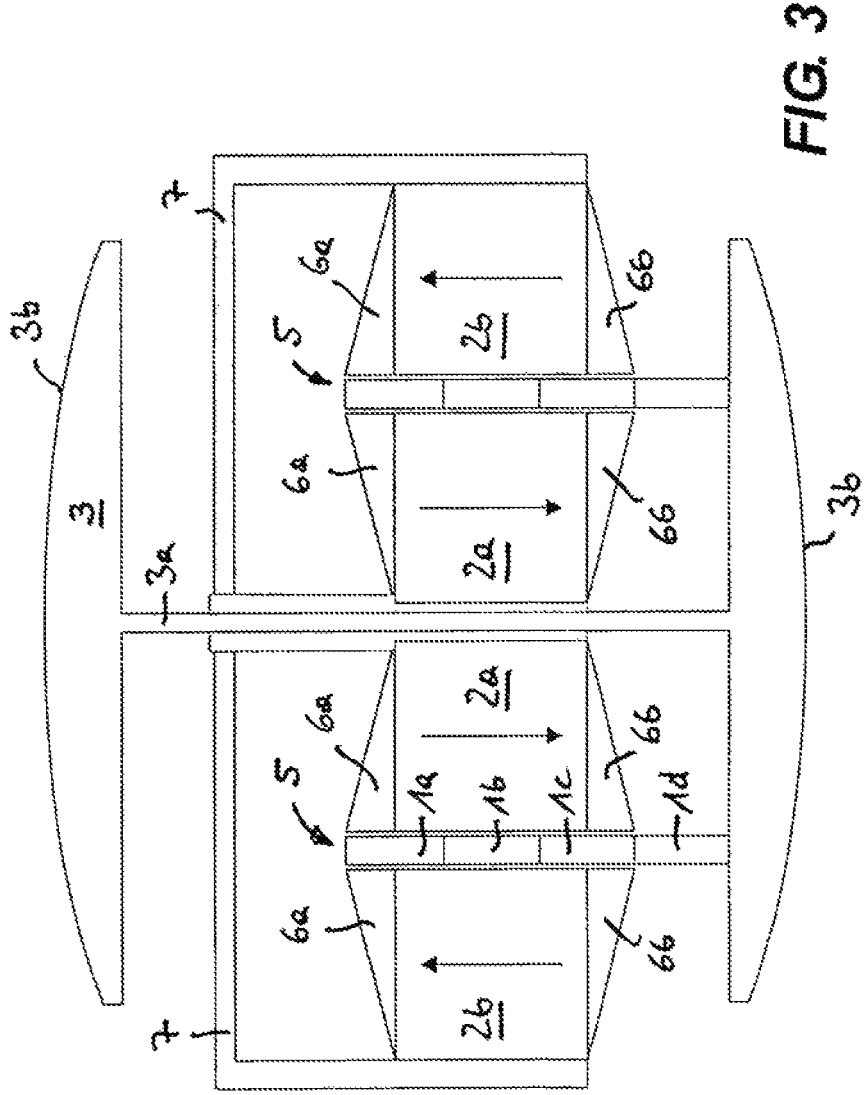

US 8,574,291 B2

LINEAR DRIVE AND PUMP SYSTEM, IN PARTICULAR AN ARTIFICIAL HEART

CROSS REFERENCE TO RELATED APPLICATIONS

This application is the US national stage of PCT application PCT/EP2008/006762, filed 18 Aug. 2008, published 26 Feb. 2009 as WO2009/024308, and claiming the priority of German patent application 102007039014.0 itself filed 17 Aug. 2007.

FIELD OF THE INVENTION

The invention concerns an electrical linear drive, in particular for a pump of an artificial heart with a movable and a stationary part, wherein the stationary part is formed by a permanent-magnet assembly and the movable part is formed by a coil assembly or vice versa, and the coil assembly and the permanent-magnet assembly can be moved to and fro relative to each other axially by current passing through the coil assembly. The invention further relates to a pump with such a drive, in particular an artificial heart for intracorporal or extracorporal assistance or the replacement of organs, in particular the heart.

BACKGROUND OF THE INVENTION

To the extent characteristics of a drive are identified in this description of the invention, they also apply to a pump, in particular to an artificial heart and vice versa.

For example, such a pump can replace the heart intracorporal as artificial heart and thus save the life of patients who have heart disease and who have previously been primarily dependent on a donor heart. Thereby, in contrast to other, previously routinely used systems, the quality of life of the patient remains preserved to a great extent.

Heart-assist systems are generally known in the prior art. A number of heart-assist systems have already been developed since the 20's and are being used in humans with increasing success. Here, a distinction is generally made between systems that assist the heart and systems that replace the heart.

When using systems that assist the heart, the heart is limited in its functionality, but can however continue to still fulfill a part of its original pumping capacity. One of the two heart chambers is connected in parallel or in series to an artificial pump that assists the heart. Under certain circumstances, a recovery of the heart can thereby be achieved and the system can then be removed.

If the natural heart is weakened so severely that assisting the heart is not enough to sufficiently supply the body with blood, and a recovery of the heart is not to be expected, the natural heart must be removed and be replaced with an alternative, for example, an artificial heart or a transplanted donor heart.

As, however, the demand for donor hearts continues to increase and simultaneously, the willingness to donate is falling, an adequate number of donor hearts is no longer available. The use of an artificial heart can reduce the high death rate of patients on the waiting list.

Systems made by Incor assist the heart and that are already used in humans. Those made by Cardiowest are used, for example, heart replacements. The individual systems assisting or replacing the heart are significantly different in their design and operation. The systems can be divided into continuously operating radial pumps or axial pumps (e.g. Incor) and pulsing reciprocating and rotary pumps (e.g. Cardiowest).

Force transmission between the drive and a pump membrane is performed by rigid mechanical connections (e.g. Abiocor 2) hydraulically (e.g. Abiocor 1), pneumatically (e.g. Cardiowest) or magnetically (e.g. Magscrew). Thereby, the transmission of force takes place in the form of a thrust or a rotational moment, either directly (e.g. Cardiowest) or through a stepdown transmission (e.g. Abiocor 2).

Particular attention is being paid to heat lost by the drive, which can damage the blood by coagulating it. By partially or completely filling the drive with cooling fluid that also serves as lubricant for storage in several concepts such as, for example, as in U.S. Pat. No. 5,300,111, an attempt is being made to dissipate heat from the blood and the surrounding tissue as homogeneously as possible.

The bearings of the pumps, conventional ball bearings and floating bearings (e.g. Abiocor 2), suffer wear or in the case of hydrodynamic bearings, e.g. as in U.S. Pat. No. 5,360,445 and magnet bearings, are largely wear-free. The trend is in the direction of low-wear drives that have a service life of at least 5 years. For a mechanical release of the bearings, rotation-symmetric drives are used in which the forces of attraction compensate as the result of centering between the stator and the rotor in rotating machines or the primary part and the secondary part in linear drives. Thus, the bearings are lighter and more compact and have longer service lives. As an ideal centering cannot be implemented technically, forces of attraction are created in all previous systems between stator and rotor or the primary part and secondary part that lead to premature wear of the bearings.

Most of what is common between the invention and prior art can be found in the electric linear drives without transmission, for example in U.S. Pat. No. 5,360,445 and U.S. Pat. No. 5,300,111.

Only when the movable parts or the fixed parts are ideally centered is a resulting force radially absent in any of the previous concepts mentioned above.

As ferromagnetic material is always used in one part and magnetic material in the other part, forces of attraction are always created between the two parts that compensate each other out only when concentric. As an ideal centering cannot be done technically, there are always more or less pronounced radial forces between the two parts. In addition to the actual guiding function, they load the bearings and lead to increased wear of the bearings, as a result of which the service life is reduced.

Previous concepts do not maximize the density of power. As described in the Panton patent (U.S. Pat. No. 5,300,111), in the development of artificial hearts the transmission of heat to the surrounding tissue and the blood can be realized by using suitable cooling steps. Rather, the weight and the dimensions of the artificial heart are the main problem of the artificial heart because of the severely limited space in the chest cavity at a specified propelling thrust. Although according to the concept of passing current as described in Gold-owsky's patent (U.S. Pat. No. 5,924,975) by selecting equally long coils and magnet segments with minimum ohmic loss, the force is maximized, but the force continues to significantly fluctuate as previously described depending on the overlap relationship and does not take on the absolute maximum value.

The reason for this is an enlargement of the magnetic field (leakage) in the sections of the adjacent coils that are not supplied with current. Thus, for ensuring a specified power, the actuation system must be configured larger than a system which would also utilize leakage flux.

The concept as in Yeakley (U.S. Pat. No. 6,194,796) uses this leakage flux by utilizing only one coil, but this long coil leads to high ohmic losses, significantly reducing the degree of effectiveness.

The magnetic flux density inside coils in all concepts is at a maximum as large as the flux density created by the magnet.

According to Lorentz, the force upon the coil through which current flows is proportional to the magnetic flux density. As a result of an increase of the magnetic flux density, for example, in the form of a flux concentrator, the force could thus be significantly increased at constant ohmic power dissipation. Thereby, an increase in the degree of effectiveness would be possible or the drive could be made smaller.

Rotary drive concepts only create a continuous speed of the flow of the blood, so that the pump behavior of the human heart it is not recreated. Likewise, in these concepts, the high speeds of rotation of the rotors are a disadvantage, in that high shear forces are exerted upon the blood that lead to increased damage of the blood.

Concepts as in Vitale (U.S. Pat. No. 6,190,409 B1) are in a position to recreate the pumping process of the human heart in its pumping capacity, however, as the result of the revolving motor within the pump, the course of the pressure stream and volume stream of the blood cannot be sufficiently recreated as in the human heart. Further, these systems sometimes work with an increased beat rate.

In the Abiocor, silicon oil is used that fills the entire drive. As no compressible medium (e.g. air) is present in the system, the membrane is actively aspirated in the diastolic phase (filling phase), as a result of which a hemodynamically unfavorable collapse of the atrium can occur.

To ensure a certain quality of life and perspective for the patient, organ-assisting or organ-replacing systems must be as quiet as possible and have a guaranteed service life of five years. All previous concepts use power converters such as mechanical, magnetic or pneumatic transmissions. The many movable parts create, however, a higher level of noise and increased wear.

OBJECT OF THE INVENTION

It is the object of the invention to provide a drive of a general type, particularly for a pump, especially an artificial heart or assist system that operates nearly free of wear and thus ensures a service life that is as long as possible, is built so compact that it can be used, for example, even as drive for an artificial heart even in smaller patients and has a pump function like physiological behavior and supplies the body with blood as much as possible physiologically, pulsing corresponding to the natural heart.

SUMMARY OF THE INVENTION

This way, the previously described disadvantages of the previous concepts are to be comprehensively avoided as much as possible, while their advantages are combined in one single system.

Particularities of the invention are, inter alia, the reduction in size so that a significant increase of the group of patients into which the system can be implanted is made possible. Further, the invention makes a longer service life of the system possible than most of the previous systems.

Further, a drive in accordance with the invention cannot only be used for actuating a pump and here, for example, as artificial heart, but for any type of drive application and especially any type of pump application.

Here the focus is especially on the pulsating transport of fluids, e.g. those that are highly sensitive relative to pressure, shear, temperature, acceleration, etc. such as for example blood. A preferred area of application of drives in accordance with the invention is thus in the area of artificial hearts, but is not limited to such.

According to one embodiment of the invention, the problem is solved by a generic linear drive that is developed further in that the coil assembly is in an air gap of the permanent-magnet assembly that extends axially, the magnetic material of which is magnetized axially and which at least at its two axial ends, is provided with inner and outer pole shoes that are opposite each other radially and spaced by the air gap, as a result of which the magnetic field in the air gap is concentrated inside opposite pole shoes radially, as a result of which at least one magnetic circuit is formed in which the magnetic field lines extend through the air gap radially from the inside to the outside, as well as through the air gap from the outside to the inside.

An arrangement of this type has the advantage that relative to conventional moving coil assemblies, the coil assemblies cannot only extend into the permanent-magnet assembly to a certain degree, but that here the air gap is open at both axial ends of the permanent-magnet assembly and thus a coil assembly can come out of both axial ends or enter into the ends. The stroke of such a drive thus depends essentially only on the axial length of the coil assembly.

Beyond that, as a result of the axial magnetization of the permanent-magnet assembly, at least one magnetic circuit results that extends axially through the permanent-magnet assembly and radially twice over the pole shoes and the air gap, namely at least at the axial ends, so that at each position at which as a result of the pole shoes the magnetic field lines are concentrated axially, there is an air gap. The coil assembly thus can pass through along the axial length of the drive, along the at least two sections (along the axial extension) of maximum field line concentrations that can be found at least at the axial ends of the permanent-magnet assembly. Between the pole shoes, on the other hand, the magnetic field is axially aligned at least essentially parallel to the axis, except for the scattered parts.

In a possible, simple embodiment of the drive in accordance with the invention the permanent-magnet assembly is subdivided axially into sections with only one permanent magnet, radially on one side of the especially in cross section frame-shaped or annular air gap, whereby on the other side of the air gap, the pole shoes are connected by material that can be magnetized, but is not itself magnetic for guiding the field lines. Thus, for example, a permanent magnet can be provided coaxially inside or outside relative to the—especially in cross section—frame-shaped or annular air gap, whereby on the other side only—especially in cross section—frame-shaped or annular pole shoes or yoke elements are provided in order to guide the field lines.

In a preferred embodiment, however, the permanent-magnet assembly has an air gap between the pole shoes and permanent magnet radially on both sides of the air gap that is especially of frame-shaped or annular section. Thus, the permanent-magnet assembly can have a first inner permanent magnet (perhaps with inner, especially coaxial passageway) and a second outer one coaxial but spaced by the air gap from the permanent magnet that is in particular of frame-shaped or annular section. This way, the axial ends of the inner and outer permanent magnet have different polarity.

A drive in accordance with the invention thus has at least two pairs of radially opposite pole shoes that are spaced by an air gap, each pair being located at an axial end. Thus, a cross-sectional shape of a pole shoe is preferred that is adapted to the cross section form of the permanent magnet with which the pole shoe is connected.

In a different embodiment between the axial pole shoes at the ends, at least one additional pair of pole shoes is provided that is opposite the other and spaced by an air gap, which concentrate the magnetic field radially. Accordingly, in such an arrangement there may not only be two radial transitions of the magnet field lines, but also three or more, as a result of which—axially—two or more magnetic circuits can be formed behind each other, and in each of the circuits the magnetic field lines extend radially once from the inside to the outside through the air gap and once from the outside to the inside through the air gap. This way, two axially adjacent magnetic circuits have a joint pair of pole shoes.

In particular in such a permanent-magnet assembly of at least two permanent magnets axially one behind the other and separated by a pole shoe applies to the coaxial inner as well as to the coaxial outer permanent-magnet assembly or to only one of the permanent-magnet assemblies, when as in the embodiment that was first mentioned, yoke material is on the opposite side.

The permanent magnets of the permanent-magnet assembly have at least one axial polarization change. In principle, any number of polarization changes is possible.

With the drive that is described here, a pump for an artificial heart can be designed favorably.

In all embodiments of such a drive, be that as pump for an artificial heart or also for any other drive application, in a further development the thickness of the pole shoes increases radially toward the air gap. As a result of this, material and thus weight can be saved. A decrease of the thickness in the direction away from the air gap is thereby harmless, as the magnetic field concentration also decreases in this direction because of the redirection of the magnetic field lines from the axial into the radial direction at the location of the pole shoes.

As it is provided in these embodiments to move the coil assembly at both axial ends of the permanent-magnet assembly out of such and into such, however, along the axial extension at least two locations are given at which the magnetic field lines run in opposite radial directions, it is provided in a further development that current passes through the coil assembly at these locations with a defined motion in a desired direction during the operation in opposite directions. For this purpose it can be provided, for example, in a simple embodiment, that the coil assembly has a single coil winding, the winding direction of which reverses at least once axially in the coil assembly. Thus, at constant current because of the reversal of the winding orientation, in practice, the reversing of the direction of current is also achieved and thus rectified driving forces are active axially between the permanent-magnet assembly and the coil assembly.

In a different, relative to this, preferred embodiment, it can be provided that the coil assembly has at least two coils or coil elements positioned axially behind each other through which different currents can flow or coils are provided, whereby in particular, by means of a controller, only those coils are supplied with current that are located inside pole shoes. Various current supplies can thereby mean different current intensity and/or direction. Hereby, the coil elements and/or pole shoes can be of different axial widths.

In all embodiments of the invention as in this embodiment the elements such as permanent magnets and pole shoes that are radially inside and outside relative to the air gap are firmly mechanically connected with each other so that their relative positions relative to each other are fixed. This can, for example, be given by a surrounding fixed frame design.

As in a different embodiment of the invention, the problem is also solved by a generic linear drive that is developed further in that the permanent-magnet assembly is designed as a stack of frame-shaped, especially annular magnets, that are alternatively radially and axially magnetized so that the magnetic field is increased on the one frame side or ring side, especially the radial outer side and on the other side, especially the radial inner side it is decreased, so that the coil assembly is coaxial to the permanent-magnet assembly on the side of the intensified magnetic field. In turn, even with such a drive, preferably, but not limiting, a pump can be designed for an artificial heart.

According to this embodiment of the invention, although a different design solution of the posed problem is used, however, as in the two embodiments, use is made of the essential idea of the invention, as a result of a special type of design of the magnetic polarization (direction of magnetization) of the permanent-magnet assembly and design environment, a local concentration of the magnetic field lines in the immediate section of the active current supply of the coil assembly is achieved. Thus, the two embodiments are connected by the same inventive idea. It is also important that in both concepts no relative motion occurs between the permanent magnet and the flow guide parts (e.g. Vacoflux).

For this, in a simple embodiment, for example, the coil assembly is provided with a single coil winding, the winding direction of which reverses at least once axially of the coil assembly. Thus, for constant supply of current because of the reversal of the winding direction, in practice, the reversal of the direction of current is also achieved and thus rectified driving forces are achieved axially that are active between the permanent-magnet assembly and the coil assembly.

In this embodiment the coil assembly is divided into individual coils and, especially by means of a controller, only those coils are supplied with current that overlap the magnetic material and/or that are primarily supplied by a radial magnetic field. This way, the power supply to the coils is switched off when the magnetic field extends essentially parallel to the axis of the linear drive. It can also be provided that the current supply to the coils is switched off when the magnetic field does not have sufficient strength. Thereby, the transition between the condition without current supply and the condition with current supply to the coils can be set to depend on the position in particular can be selected continuously and, e.g. be done by means of a controller.

In the two embodiments of the invention a current supply of the coil assembly is realized, e.g. by sliding contacts and especially preferred, by at least two electrical conductors that are designed helically. In a defined position, the conductors can form a spiral that lies in a plane so that as a result of a deflection of the coil assembly relative to the permanent-magnet assembly, the inner or outer end of the respective spiral then moves out of this plane. Hereby the affected helical conductor lies on an imaginary cone-shaped shell.

Here the at least two conductors can helically surround each other in a plane and/or at least two conductors are located layered in a spiral with intermediate insulation. In particular, in the case of a layered arrangement, several conductors layered in a spiral can start and/or end with an offset in the spiral direction in order to be able to attach the electrical supply at the offset ends more easily.

The design of the input leads as helical conductors has the particular advantage that an end of these conductors can be fastened to a fixed element of the drive and the other end to a moving part, e.g. the coil assembly. In a relative motion of the parts toward each other, the helical conductors move out of the spiral plane without generating much mechanical stress. Conductors that are designed in this manner thus have a long service life, which is especially important in the application for artificial hearts.

The number of the helical conductors can be limited to two, when electronics (power converter) for supplying current to and for switching of coils are located at the coil assembly itself and thus, for example, also moved along. Then, only the two input leads for this electronic unit are needed.

The coil assembly itself can be fastened to a force-transmission element formed in a middle section, especially coaxially, in the permanent-magnet assembly and that extends through the permanent-magnet assembly. Thus, a space-saving arrangement is possible. The coil windings can, for example, be located to a support element that is designed, for example, pot-shaped and where the force-transmission element is located.

The force-transmission element can be provided with pressure disks located axially on both sides of the permanent-magnet assembly, by means of which a force can be exerted against surrounding elements, especially a membrane of the pump chamber.

BRIEF DESCRIPTION OF THE DRAWING

The relevant prior art and embodiments of the invention are shown in the following figures. Therein:

FIG. 3 shows a linear drive according to the first embodiment, e.g. for use in an artificial heart;

DETAILED DESCRIPTION

Figure 1:
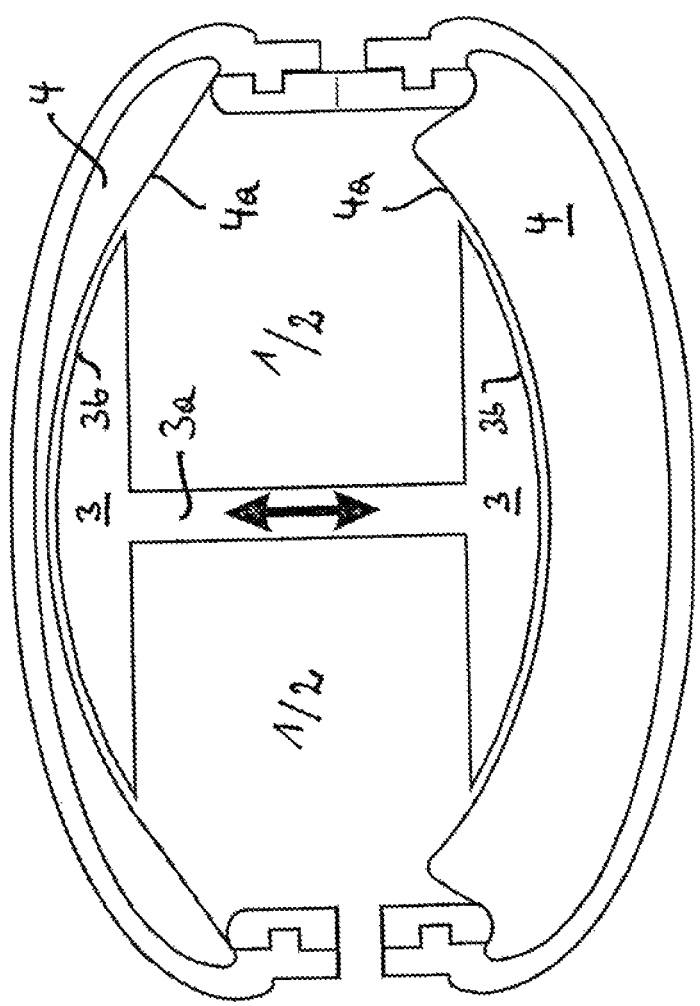
FIG. 1 shows a prior-art artificial heart with a linear drive.

In conjunction with FIG. 1, the main characteristics of a pump, for example, for an artificial heart with a linear drive are discussed, the linear drive with its coil and permanent-magnet assembly not being shown. The pump that is shown here schematically can house linear drives as in both embodiments of the invention.

All linear drive system have in common that the movable part comprises a coil assembly 1 with at least one coil and the stationary part with at least one permanent magnet 2 or vice versa. The permanent magnets 2 generate a magnetic field with flow density B. It penetrates the coils 1 completely or proportionately. In FIG. 1, the references 1 and 2 are located only symbolically as the location that holds the drive, without specifically describing coils 1 and magnets 2.

As a result of the flow a current I in coils 1 of the coil assembly, a force F is exerted as in Lorentz onto coils 1 with medium winding length l and the winding number n as in $$\vec{F} = n \cdot I \cdot (\vec{l} \times \vec{B})$$

This force is transmitted through a mechanical, hydraulic, pneumatic or magnetic force-transmission element 3 to at least one pump chamber 4, preferably alternately transmitted to two pump chambers 4 positioned on both axial ends of the linear drive. Each pump chamber can have a membrane 4a on its inner wall on which the force-transmission element 3 acts when moving and thus displaces for example blood from the chamber 4 on the one side so that blood flows into the chamber 4 of the other side. So that the force-transmission element 3 can be displaced by current passing through the coil assembly, the coil assembly or the magnet assembly is mounted on this force-transmission element 3, for example, at a winding support that is on the force-transmission element 3.

The movable parts are carried on floating bearings or ball bearings, magnetic bearings or hydrodynamic bearings that engage for example an axial part 3a of the force-transmission element 3. By reversing the direction of current in the coils, the direction of the force is reversed so that a pulsating effect is created in the pump chambers 4. Valves at the inlets and outlets define the direction of flow of the fluid, especially blood. By the amplitude of the current in the individual coils, the current and thus the speed of the flow of the fluid and the pulse can be regulated.

Figure 2A:
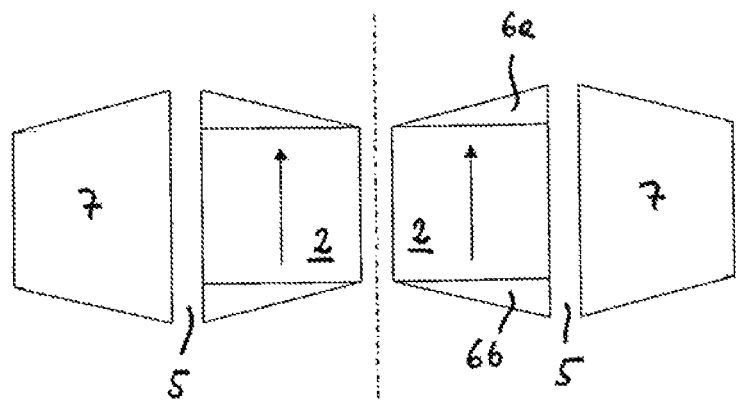
FIGS. 2a, 2b, and 2c show permanent magnets and pole shoe elements without the coil assembly according to a first embodiment of the invention.
Figure 2B:
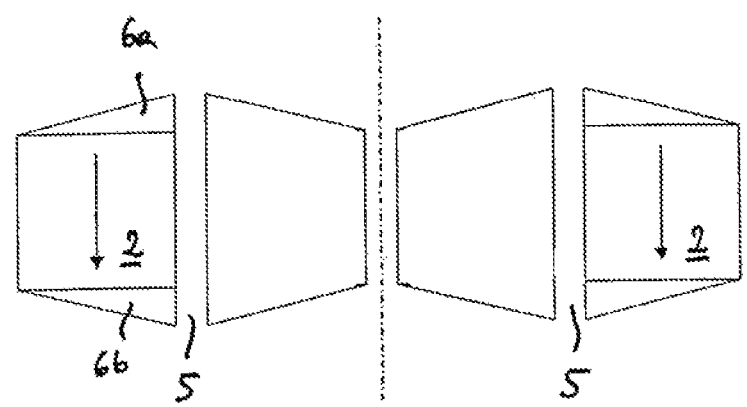
Figure 2C:
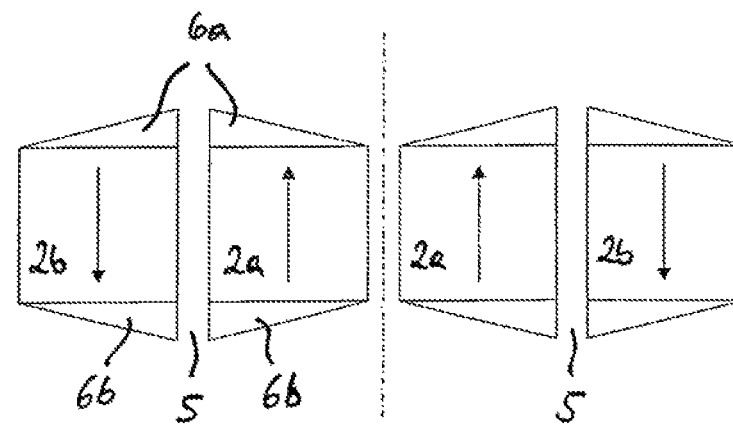

FIGS. 2a-2c show various variants of a first embodiment of the invention.

Figure 4:
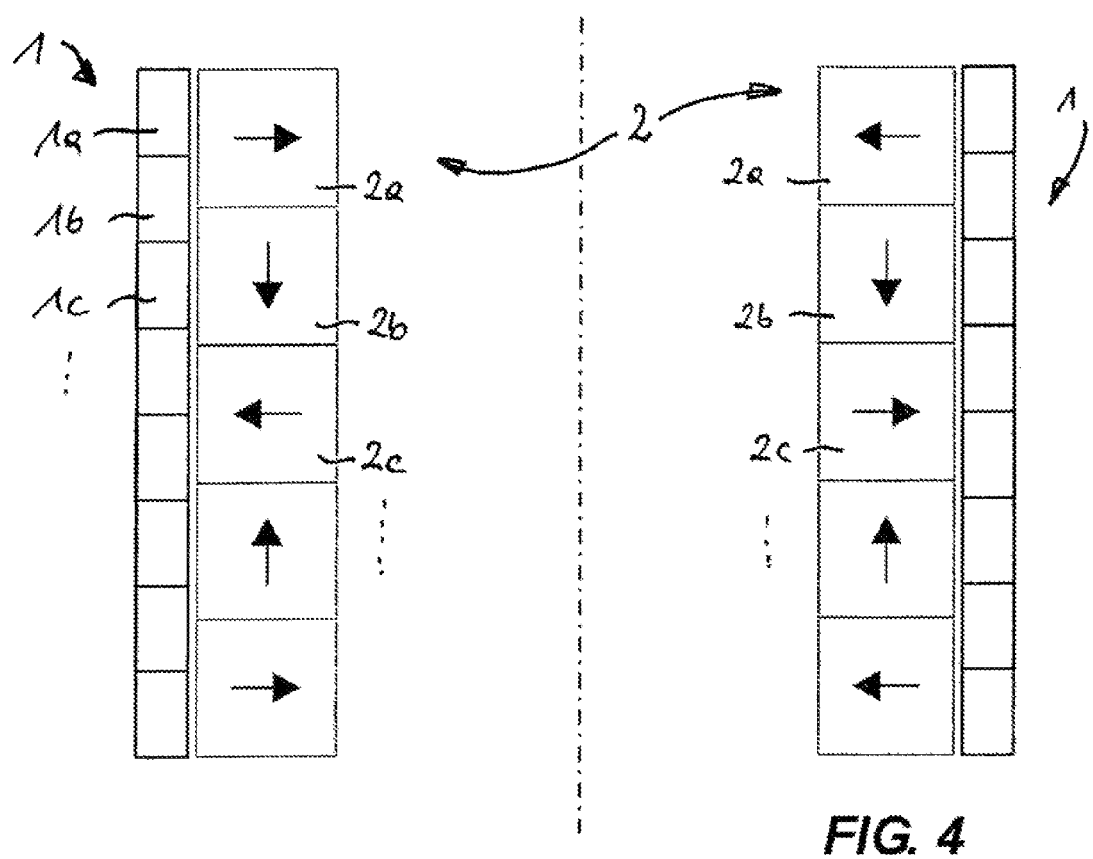
FIG. 4 shows a permanent-magnet and coil assembly according to a second embodiment of the invention.

In FIG. 2a an axially polarized permanent magnet 2 is coaxially inside relative to an air gap 5. The permanent magnet materials are shown by arrows and the direction of magnetization are indicated by the directions of the arrows. Here, the permanent magnet 2 is annular with an axial aperture through which, for example, a force-transmission element 3 can be passed and at which the corresponding bearing for the force-transmission element can be realized. Neither is shown here in the interest of simplifying the view. The dotted line shows a symmetry axis in FIGS. 2a-2c, especially a rotation-symmetry axis that is shown in FIGS. 3 and 4.

On the two axial (here upper and lower) ends of the permanent magnet pole shoes 6a and 6b (FIG. 3), in particular of frame-shaped or annular pole cross section are provided and firmly connected with the permanent magnet 2 in order to radially redirect the axial magnetic field of the permanent magnet 2 and to concentrate it radially.

At a radial spacing around the permanent magnet 2, a frame-shaped or annular yoke element 7 is located that is made of a magnetizable, however not itself magnetic material. As a result of the spacing, a frame-shaped or annular air gap 5 is formed around the symmetry axis and holds a coil assembly not shown here. In the pole shoes 6a and 6b, as well as in the yoke element 7, the shape is such that its thickness increases radially toward the air gap 5.

With reference to FIG. 2a, the magnetic field lines extend from the bottom to the top for the inner permanent magnet 2, through the upper pole shoe 6a radially from inside to outside, back down in the yoke element 7 and through the lower pole shoe 6b radially from outside to inside. Thus, a closed magnetic circuit results in which the radially concentrated magnetic field lines penetrate the air gap 5 twice but in different directions.

This is the essential difference in this arrangement relative to conventionally known plunger coil prior-art assemblies in which the moving coil assembly is penetrated radially by the magnetic field in only one direction. The coil assembly not shown here can thus be moved into and out of the drive on both axial ends.

Unlike FIG. 2a, in FIG. 2b, the permanent magnets 2 with pole shoes 6a and 6b and yoke element 7 have been switched. Otherwise, the operating mode and the directions of the field lines are identical.

A preferred embodiment is shown in FIG. 2c, where purely axially magnetized permanent magnets 2a and 2b are on both sides of the air gap 5 with the magnetization of the inner and outer permanent magnets opposite each other. Both permanent magnets 2a and 2b carry pole shoes 6a and 6b at their axial ends, and the pole shoes are separated by the air gap 5 from the inner and outer magnet 2a and 2b and are positioned radially opposite each other. Here, the same magnetic circuit results as in FIGS. 2a and 2b, but with larger magnetic field strength because of the two permanent magnets. Here too, the field is radially concentrated at the axial ends so that the here unillustrated coil assembly 1 is essentially traversed by the magnetic field only at the axial ends of the pole shoes, while the more central axial regions do generate stray fields that are essentially negligible.

FIG. 3 shows a linear drive with an arrangement of magnets 2a and 2b and pole-shoe pairs 6a and 6b as in FIG. 2c. Here, the coil assembly 1 has, for example, four coils 1a, 1b, 1c, and 1d in the air gap 5 between the two permanent magnets 2a and 2b, that are magnetized axially but opposite each other.

As a result of the use of pole shoes 6 that are preferably provided with high magnetic saturation induction, the field in the gap 5 is strongly concentrated in the pole shoes 6. Because of the use of field-concentrating pole shoes 6, a greater field is generated compared with all previous concepts since as in $$\vec{F} = n \cdot I \cdot (\vec{l} \times \vec{B})$$

at constant power, a smaller coil current is sufficient. Thus, the ohmic power dissipation, which is proportional to the square of the current is significantly reduced: P is proportional to $1/B^2$.

As a result of the nonferrous design of the movable or stationary part, no Maxwellian forces of attraction are created between the two parts. Thus, the bearings that carry the coil assembly 1 by means of the force-transmission element 3 at the inner permanent magnet 2a are relieved radially and can be dimensioned smaller or be optimized for a long service life. The outer magnet 2b is mechanically fixed on the inner magnet 2a, here by the elements 7. Here, the force-transmission element has an inner axis 3a in an inner coaxial passage through the inner magnet 2a. Any other type of support is also possible. It is only important that as a result of supplying current to the coil assembly, the force-transmission element 3 can be moved in two directions.

A further advantage of the nonferrous design of one of the two parts inherently makes it possible that one part can be moved out of the other part without generating Maxwellian forces of attraction between the two parts. Thus, by an adaptation of the length relationship between the fixed and movable part, the power profile can be adapted to a required power profile, for example, that of the human heart, and thus weight and construction size can be reduced.

To minimize ohmic losses, the coil assembly here comprises individual coils that can be supplied with current 1a, 1b, 1c, and 1d (here by way of example, 4 coils), whereby in accordance with the invention only those coils are supplied with current that juxtaposed with the pole shoes 6a or 6b. The other coils do not contribute to the power and can therefore remain without current.

For all possible embodiments that are shown here or not shown here, the individual supplies of current can be provided by a controller that can, for example, be provided directly on the coil assembly and only receives its current supply from the outside or can also be located outside the drive. The supply of current to a coil that is between the pole shoes 6 can take place in every embodiment, for example, depending on position, automatically by the controller. In order to determine the position, a position sensor can be provided that captures the position of the coil assembly and/or of the force-transmission element relative to the pole shoes or the permanent magnet. A light curtain can be provided, for example, in order to capture a defined zero position and a motion sensor for capturing the direction and extent of movement such as is known, for example, from optical computer mice. Likewise, position capture can take place, for example, directly by the controller without any sensors. By selecting the coils and pole shoes axially with different widths, leakage flux for generating can likewise be used.

The drive described here can, when used in a pump as shown in FIG. 1, ideally recreate the pumping cycle of the human heart in all described embodiments. This avoids active suction of membrane 4a during diastole, when the force-transmission element 3 only loosely contacts the membrane 4a with its pressure disks 3b. The support of the movable part relative to the fixed part can, for example, take place by conventional bearings such as ball bearings or floating bearings, or completely friction-free by means of hydrodynamic or magnetic bearings.

Figure 5:
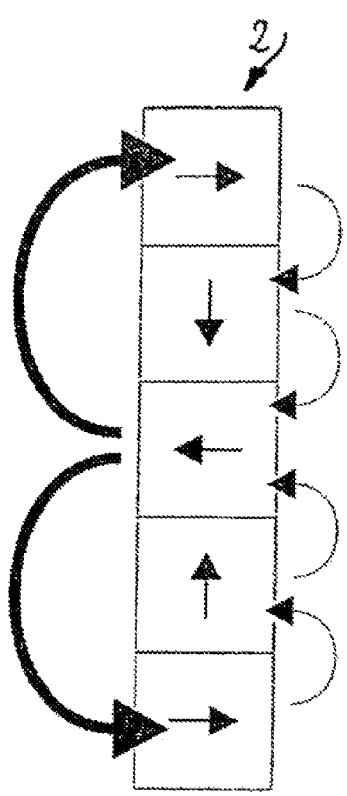
FIG. 5 is a view illustrating the principle of the concentration of the magnetic field lines in a second embodiment of the invention.

FIG. 4 shows a drive consisting of the permanent-magnet assembly 2 and the coil assembly 1 as in the second embodiment of the invention. Here, the magnet assembly 2 is comprised of a row of magnets that are oriented perpendicular to each other, especially alternating several times, axially and radially, axially. Permanent magnet rings 2a, 2b, 2c, . . . can, for example, be stacked on each other with alternating axial and radial magnetization. Thus the progression of the field lines shown in FIG. 5 results, with the field strengthened on the left (outer) side of the magnetic material 2, and weakened on the other (inner) side. Differently orienting the magnet rings, can achieve the reverse effect.

In accordance with the invention the coil assembly 1 is in a strengthened magnetic field, here radially outside. No Maxwellian forces of attraction are created between the magnet assembly 2 and the coil assembly 1, as a result of which the baring is not loaded mechanically radially. Here too, a force-transmission element as shown in FIG. 1 can carry the coil assembly 1 and be extend through the inner free passage of the magnet assembly 1.

Further, by use of the preferred thin—not shown here—back iron yoke within the magnet assembly 2, stray fields can be decreased further and the magnetic field in the coils can be increased further. Even this does not have any effect on the radial bearing load.

Likewise, because of the absent Maxwellian forces of attraction, the movable part can be moved out of the stationary part without the occurrence of return forces. Thus it is possible to adapt the drive by the selection of a suitable length relationship of magnet and coils to a required power profile, for example that of an artificial heart.

As a result of a preferred subdivision of the coil assembly 1 into individual coils (coil rings located axially behind one another) 1a, 1b, 1c, . . . for decreasing the ohmic losses, only those coils are supplied with current that are juxtaposed with the magnetic material 2. This way, those coils in the magnet assembly 2 are simultaneously switched off from the current supply, where the magnetic field extends parallel to the axis, i.e. here, for example, in the permanent magnetic ring 2b. This individually supplied current can in turn be done by a controller, perhaps with position capture, for which the same applies as was described for the invention as in the first embodiment.

Because of a position-dependent, continuous transition between a condition without current supply and a condition with current supply, the field parts can be utilized optimally for generating a radial propelling thrust at minimal ohmic power dissipation.

By choosing a different length relationship of magnet segment (ring 2a, 2b, . . . ) to coil 1a, 1b, . . . the leakage flux is also optimally utilized for power generation. By using individual, independent power supply to the coils, all previously listed disadvantages are avoided so that this concept recreates the human heart in a pump drive in all identified embodiments.

In addition to an adaptation of the blood pressure and the volume stream during a pumping cycle, the active suction of the membrane in diastole is prevented, since the male membrane 3b of the force-transmission element 3 as in FIG. 1 is not firmly connected with the membrane 4a. Accordingly, the membrane 4a is moved backward only as the result of the natural blood pressure so that the danger of a collapse of the atrium is no longer present.

Noise development is minimal because of the lack of Maxwellian forces of attraction between the stationary and the movable part, the low relative speed between the individual parts by using a direct drive, as well as bearings that are not exposed to any interfering forces.

Support of the movable part relative to the stationary part can also be accomplished here, for example, by conventional bearings such as ball bearings or floating bearings or completely friction-free, by means of hydrodynamic bearings.

Because of the ability to pass current to the individual coils in both embodiments of the invention, an increased redundancy of the drive is also given. Failures of coils or electronic parts do not lead to a complete failure of the system but only to a decrease of the attainable delivery volume. The special embodiment of this concept relative to the prior art is, that the system in accordance with the invention that supports organs or replaces organs reduces the disadvantages of the actual systems to a minimum, while it combines the advantages of the individual concepts in a single system.

Figure 6:
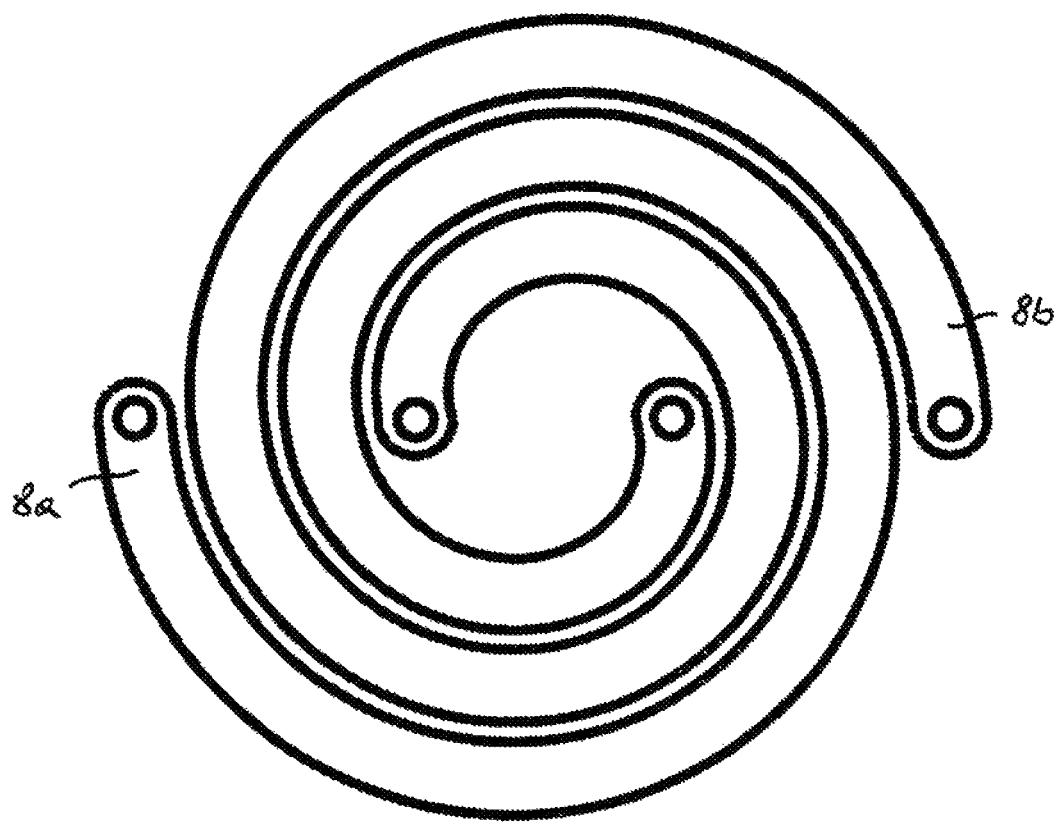
FIG. 6 shows two helically extending electric conductors for contact between a coil assembly and a permanent-magnet assembly that move relative to each other.

It applies to all possible embodiments that when the coils form the movable part, the current supply, for example by sliding contacts, can take place inductively or in a spring system shown in FIG. 6. Here, only two conductors 8a and 8b are shown by way of example that respectively extend helically and thereby surround each other in order to achieve an electrical contact from the radial inside to the radial outside. Thus, here an outer end of conductors 8a and 8b can be fastened at a part of the drive (e.g. magnet part) and the inner end at the other part of the drive (e.g. coil part). In the case where the coils form the stationary part, these contacts can be dispensed with completely. Thus, the number of moving parts and parts subject to wear and tear is reduced further.

As a result of the integration of a converter as control device into the movable part, for example the coil assembly, the number of springs can be limited to two, however, several springs per converter are also possible.

As a result of the separate supply of current to the coils, the drive has increased redundancy. Failures of coils or electronic parts do not lead to a complete failure of the system, but only to a decrease of the maximum attainable blood pressure.

Concerning all embodiments it is noted that the technical characteristics identified in connection with one embodiment cannot only be used in the specific embodiment, but also in the other embodiments. All revealed technical characteristics of this description of the invention are to be ranked as essential to the invention and can be combined with each other in any way or used individually.

The invention claimed is:

1. An electric linear drive for a pump, the drive comprising:
a stationary part;
a movable part, one of the parts being formed by a permanent-magnet assembly having, relative to an axis, an axially polarized inner permanent magnet and an axially polarized outer permanent magnet each having a pair of axially opposite ends and together forming an axially extending air gap, the other of the parts being formed by a coil assembly having a single winding whose orientation reverses at least once axially;
respective inner and outer pole shoes at the axial ends of the inner and outer permanent magnets and axially spaced at the air gap such that the pole shoes concentrate a magnetic field of the permanent magnets in the air gap and a magnetic circuit is formed such that at one axial end of the permanent magnets the magnetic field lines extend through the air gap radially from the inside to the outside and at the other axial end through the air gap from the outside to the inside; and
a force-transmission element extending in the air gap and connected to the movable part and to at least one pump chamber, whereby when an electrical current is applied to the coil assembly the element is shifted axially.

2. The linear drive according to claim 1, wherein the permanent magnets are radially on both sides of the air gap and between the pole shoes.

3. The linear drive according to claim 2, wherein the permanent magnets are in cross section frame-shaped or annular.

4. The linear drive according to claim 1, wherein the pole shoes concentrate the magnetic field radially at an axial end of the permanent magnet assembly.

5. The linear drive according to claim 1, wherein one of the permanent magnets of the permanent-magnet assembly is provided with at least one axial polarization change.

6. The linear drive according to claim 1, wherein a thickness of the pole shoes increases radially toward the air gap.

7. The linear drive according to claim 1, wherein the winding of the coil assembly has at least two coils that are positioned behind each other axially and can be variously supplied with current, only those coils being supplied with current being inside the pole shoes.

8. The linear drive according to claim 1, wherein the coil assembly or pole shoes have different axial widths.

9. The linear drive according to claim 1, wherein the coil assembly can simultaneously be switched off from a current supply when the magnetic field is not sufficiently strong.

10. A linear drive for a pump for an artificial heart, the linear drive comprising:
a stationary part;
a movable part spaced from the stationary part and forming therewith an air gap extending along an axis, one of the parts being formed relative to the axis by a stack of annular permanent magnets that are alternately radially and axially magnetized so that a resultant magnetic field on one side of the stack of annular permanent magnets is strengthened and on the other side is weakened, the other of the parts being formed by a coil assembly mounted coaxially on the stack of annular permanent magnets on the one side of the stack of annular permanent magnets and formed by individual coils; and
a force-transmission element extending axially in the air gap and connected to the movable part and to at least one pump chamber; and
means for supplying electrical current only to those coils axially overlapping the stack of annular permanent magnets so as to shift the force-transmission element axially.

11. The linear drive according to claim 10, wherein the coils can simultaneously be switched off from a current supply, the magnetic field extending essentially parallel to the axis.

12. The linear drive according to claim 10, wherein a transition between a condition without current and a condition with current of the coils is position-dependent and can be adjusted continuously.

13. The linear drive according to claim 12, further comprising:
 a controller for supplying the current to coils of the coil assembly depending on position.

14. The linear drive according to claim 13, further comprising for determining an actual position of the coils:
 at least one sensor for determining an original position or a sensor particularly for optically determining a direction of movement or amplitude of movement of the coils.

15. The linear drive according to claim 10, wherein the coil assembly is fastened to the force-transmission element that is mounted in a middle section coaxially in the stack of annular permanent magnets and that extends through the stack of annular permanent magnets.

16. The linear drive according to claim 15, wherein the force-transmission element is provided axially on both sides of the stack of annular permanent magnets with pressure disks that can apply a force to a membrane of a pump chamber.

17. A linear drive for a pump for an artificial heart, the linear drive comprising:
 a stationary part;
 a movable part forming with the stationary part an air gap extending along an axis, one of the parts being formed relative to the axis by a stack of annular permanent magnets that are alternately radially and axially magnetized so that a resultant magnetic field on one side of the stack of annular permanent magnets is strengthened and on the other side is weakened, the other of the parts being formed by a coil assembly mounted coaxially on the stack of annular permanent magnets on the one side of the stack of annular permanent magnets;
 a force-transmission element extending axially in the air gap and connected to the movable part and to at least one pump chamber; and
 supply means including at least two helical electrical conductors for feeding an electrical current to the coil assembly to shift the force-transmission element axially.

18. The linear drive according to claim 17, wherein the conductors surround each other helically in one plane.

19. The linear drive according to claim 17, wherein the conductors are layered in a spiral with intermediate insulation.

20. The linear drive according to claim 19, wherein the conductors start or end with an offset.

* * * * *